US007186401B2

(12) United States Patent
Keller et al.

(10) Patent No.: US 7,186,401 B2
(45) **Date of Patent: *Mar. 6, 2007**

(54) DRY POWDER FOR INHALATION

(75) Inventors: Manfred Keller, Bad Krozingen (DE); Rudi Müller-Walz, Schopfheim (DE)

(73) Assignee: Jagotec AG, Muttenz (CH)

(*) Notice: Subject to any disclaimer, the term of this patent is extended or adjusted under 35 U.S.C. 154(b) by 0 days.

This patent is subject to a terminal disclaimer.

(21) Appl. No.: 10/628,965

(22) Filed: Jul. 28, 2003

(65) Prior Publication Data

US 2004/0202616 A1 Oct. 14, 2004

Related U.S. Application Data

(63) Continuation of application No. 09/831,011, filed as application No. PCT/CH99/00528 on Nov. 10, 1999, now Pat. No. 6,645,466.

(30) Foreign Application Priority Data

Nov. 13, 1998 (CH) .................................... 2286/98

(51) Int. Cl.
*A61K 9/12* (2006.01)
*A61K 9/14* (2006.01)
*A61M 11/00* (2006.01)

(52) U.S. Cl. ........................... 424/43; 424/45; 424/46; 424/489; 514/177

(58) Field of Classification Search .................. 424/43, 424/45, 46, 434, 400, 489; 128/200.14, 203.12; 514/177
See application file for complete search history.

(56) References Cited

U.S. PATENT DOCUMENTS 6,182,655 B1 * 2/2001 Keller et al. ........... 128/203.15
6,645,466 B1 * 11/2003 Keller et al. .................. 424/43

FOREIGN PATENT DOCUMENTS

| | | | |
|---|---|---|---|
| EP | 0 416 950 | | 9/1990 |
| EP | 0 416 951 | | 9/1990 |
| WO | WO 93/11773 | | 6/1993 |
| WO | WO 9915182 | * | 4/1999 |
| WO | WO 00/53157 | | 9/2000 |

OTHER PUBLICATIONS

Adjei and Gupta, In *Inhalation Delivery of Therapeutic Peptides and Proteins*, Adjei and Gupta eds., Marcel Dekker, Inc., New York, 1997, Chapter 22, pp. 625-637.
Bolhuis and Lerk (1981). *J. Pharm. Pharmacol. 33*: 790.
Braun et al. (1996). *Int. J. Pharm. 135*: 53-62.
Byron, In *Respiratory Drug Delivery*, Byron ed., CFC Press, Inc., Boca Raton, 1990, pp. 169-170.
Chowhan and Chi (1986). *J. Pharm. Sci. 75*: 534-541.
Ganderton (1969). *J. Pharm. Pharmac. 21*: 9S-18S.
Geuns et al. (1997). *European J. Pharm. and Biopharm. 44*: 187-194.
Handbook of Pharmaceutical Excipients, 2nd ed., 1994, pp. 280-282.
Hickey et al. (1994). *Pharma. Tech.* pp. 58, 60, 62-64, and 82.
Mahmoud and El-Shaboury (1985). *Acta. Pharm. Fenn. 94*: 125-131.
*Martindale: The Extra Pharmacopeia*, 28th ed., Reynolds ed., The Pharmaceutical Press, London, 1993, Abstract 6022-f.
Meakin et al. (1995). *Int. J. Pharm. 119*: 103-108.
MIMS (Monthly Index of Medical Specialties), Nov. 1996, pp. 244-245.
MIMS (Monthly Index of Medical Specialties), Oct. 1998, pp. 271-273.
Murthy and Samyn (1977). *J. Phar. Sci. 66*: 1215-1219.
Note for Guidance on Development Pharmaceutics, European Agency for the Evaluation of Medicinal Products, Human Medicines Evaluation Unit, CPMP/QWP/155/96, Jan. 28, 1998.
Note for Guidance on Dry Powder Inhalers, European Agency for the Evaluation of Medicinal Products, Human Medicines Evaluation Unit, CPMP/QWP/158/96, Jun. 24, 1998.
Peart et al. (1997). *Pharm. Res. 14*: S-142-S-143, Abstract No. 1405.
*Pharmaceutics: The Science of Dosage Form Design*, ed. Michael E. Aulton, Churchill Livingstone, Edinburgh, London, Melbourne and New York, 1988, p. 56.
Price et al. (2002). *Int. J. Pharm. 246*: 47-59.
*Remmington's Pharmaceutical Sciences*, 18th ed., 1990, Chapter 31, pp. 589-593, and 602; Chapter 76, pp. 1451-1452; and Chapter 89, pp. 1633, 1636, and 1637.
*Respiratory Drug Delivery II*, paper presented by John N. Staniforth at a meeting in Keystone, CO, Mar. 26-30, 1990.
Statutory Declaration from Professor David Ganderton, Dec. 15, 2003, In the Matter of an opposition by Vectura Limited to EP 1 131 059 in the name of Jago Research AG.
van Kamp et al. (1986). *Pharm. Acta. Helv. 61*: 22-29.
Young et al. (2003). *J. Pharm. Sci. 92*: 815-822.
Zeng et al., In *Particulate Interactions in Dry Powder Formulations for Inhalation*, Taylor and Francis, Inc., New York, 2001, Sections 1.6.7 (pp. 23-24) and 5.5.6. (pp. 163-165).

* cited by examiner

*Primary Examiner*—Johann Richter
*Assistant Examiner*—Mina Haghighatian
(74) *Attorney, Agent, or Firm*—Ivor R. Elrifi, Esq.; Naomi S. Biswas, Esq.; Mintz Levin

(57) ABSTRACT

The aim of the invention is to improve the moisture resistance of dry powder formulations for inhalation which contain a pharmaceutically ineffective carrier of not-inhalable particle size and a finely divided pharmaceutically active compound of inhalable particle size and to also improve the storage stability of said formulations. To this end, magnesium stearate is used in said formulations. One of the features of the inventive dry powder is that a high fine particle dosage or fine particle fraction can be maintained also under relatively extreme temperature and humidity conditions.

28 Claims, No Drawings

DRY POWDER FOR INHALATION

CROSS REFERENCE TO RELATED APPLICATION

This application is a continuation of U.S. patent application Ser. No. 09/831,011 filed Aug. 9, 2001, now U.S. Pat. No. 6,645,466 which is the National Stage of International Application No. PCT/CH99/00528 filed Nov. 10, 1999.

FIELD OF THE INVENTION

The invention relates to the improvement of the resistance to moisture of dry powder formulations for inhalation, and to the novel dry powder formulations.

BACKGROUND OF THE INVENTION

Dry powder formulations for inhalation must fulfil a number of demands which are partially contradictory to one another, where the following, in particular, are to be taken into account:

The active compound must be inhalable. In order to be able to pass into the lungs, it must be present in particles of size about 1 to 10 μm. Such microfine particles can be obtained, for example, by micronization, controlled precipitation from suitable solvents or by spray drying if the process conditions are suitably selected, controlled and carried out. Microfine particles, however, have a very unfavorable, i.e. large, ratio of surface to volume or mass and therefore a large surface energy. This is manifested in strong adhesion and cohesion tendencies which in turn lead to poor flow properties and to powder aggregation. Microfine powders of this type are therefore difficult to handle and are strongly influenced by electrostatic charge, processing, atmospheric humidity and the like.

In order to guarantee consistent production of the formulation, mechanical filling of the powder inhaler and correct dosage and release by the powder inhaler, the powder must be free-flowing. Good flow properties are as a rule expected with sufficiently large particles which are as spherical as possible and which have a low surface energy and small contact areas.

In the case of powder inhalers having a reservoir, the finished pharmaceutically preparation is filled into the reservoir in the form of a powder bed. A dose is withdrawn by means of a suitably designed dosage device. Withdrawal takes place volumetrically. The accurate volumetric dosage of the preparation for most active compounds necessitates dilution thereof with a pharmaceutically inactive excipient in order to obtain a dosable unit amount meeting the demands on dosage accuracy.

For powder inhalers which release the medicament from predosed units, e.g. capsules or blister packs, the same restriction applies for the frictionless operation of the filling machines for these unit doses.

In the case of a multidose dry powder inhaler which contains a powder reservoir from which the individual doses are withdrawn by means of a dosage mechanism, as a rule the pulverulent medicament is in contact with the surrounding area and can thus be influenced by atmospheric humidity. The quality of the medicament and of the inhalation system must not be significantly adversely affected, however, by the influence of external factors during the intended storage time and up to the use of the pack.

In order to meet these requirements, the inhalable, i.e. present in microfine particles, constituents (active compounds) are mixed with pharmacologically inactive substances in order to obtain flowable powders. The dilution is chosen here such that the amount applied from the powder inhaler exactly contains the desired dose. The predominant proportion of the pharmacologically inactive excipient is present here intentionally in a particle size which is not inhalable. It serves not only for dilution, but also for establishing an acceptable, if possible a good to very good, flowability of the powder mixture. In the case of these "interactive or ordered mixtures", it is the carrier substance, to which the microfine active compound particles are bound by adhesion in order to achieve and to maintain a suitable mixed material, i.e. homogeneity of the mixture. By means of the mixing process, the particle size of the carrier can also be changed such that a certain proportion is inhalable. The particle size of the carrier employed in this case as a rule depends on the requirements and specifications of the powder inhaler which is intended for the administration of the formulation. It is true for these mixtures that during all required processing, transport, storage and dosage operations no demixing must take place, i.e. the active compound particles must not detach from their carrier particles. During dispersion in the inhaler, induced by the respiratory flow of the patient, the active compound particles, however, must be detached as effectively as possible, i.e. as quantitatively as possible, in order to be inhaled. The carrier is in most cases lactose, but can also be mannitol, trehalose or another suitable carrier material. In some inhalers obtainable on the market, glucose is also present as a carrier material.

It is known that the flow properties of ordered mixtures in the main depend on the physicochemical properties of the carrier, which in fact as a rule is admixed in an excess. It is likewise known that the effectiveness of the release of the inhalable primary particles of the active compound by shearing force especially also depends on the properties of the carrier, in addition to the physicochemical, substance-specific properties of the active compound and the physical, in particular aerodynamic, properties of the powder inhaler. For this purpose, as an analytical parameter, the amount of active compound in fine, inhalable particles (fine particle dose, subsequently also designated by FPD) or the fine particle fraction (subsequently also designated by FPF) is determined relative to the total amount of released active compound in vitro in so-called cascade impactors or liquid impingers, such as are described in various pharmacopeias.

Recent studies show that the FPF is all the higher, the smaller the particle size of the admixed lactose [M. J. Clarke, U. J. Potter, P. Lucas, M. J. Tobyn and J. N. Staniforth: Poster presentation to the conference "Drug Delivery to the Lungs VIII" of the Aerosol Society, London, 12.15–16.1997; and P. Lucas, M. J. Clarke, K. Anderson, M. J. Tobyn and J. N. Staniforth (1988): Presentation to the conference "Respiratory Drug Delivery VI", Hilton Head Island, 5.3–7.1998, published in: R. N. Dalby, P. R. Byron and S. J. Farr (editors): Respiratory Drug Delivery VI, Interpharm Press, 1998, 243 et seq.]. This process, however, comes up against a natural barrier, as the flowability with smaller particles rapidly becomes inadequate.

It was likewise shown that on comparison of identical screen fractions of various lactose grades a recrystallized lactose achieved the higher FPF [N. M. Kassam and D. Ganderton: J. Pharm. Pharmacol. 42 (1990), 11 et seq. (Suppl.) and EP-B-0 464 171]. This effect is based on the fact that the active compound particles preferably adhere to defects, cracks and breaks, i.e. to particularly activated centers ("active sites" or "hot spots") of the carrier particles. The adhesion forces are largest at these activated centers and thus the detachment is also least probable during inhalation. It was then shown by electron micrographs that the recrystallized lactose is very much more regular than the commercially available material.

It is furthermore known that crystalline α-lactose monohydrate also contains a small proportion of amorphous lactose which interferes with the regular crystal structure and thus provides activated sites on the crystal surface [G. Buckton and P. Darcy: Int. J. Pharm. 123 (1995), 265 et seq.; E. M. Phillips: Int. J. Pharm. 149 (1997), 267 et seq.]. In the case of increased atmospheric humidity, water can preferably add to these amorphous centers and, as a plasticizer, cause a conversion into the thermodynamically more stable crystal form [B. C. Hancock and G. Zografi: J. Pharm. Sci. 86 (1997), 1 et seq.]. In turn, this has the result that the storage stability of powder preparations of this type is limited at increased atmospheric humidity.

In WO-A-95/11666, it was proposed to saturate the active centers by addition of microfine lactose with the aim of making available only a few energy-rich binding sites on the lactose to the active compound in the preparation of the final mixture. Since detachment during inhalation accordingly needs less energy, the FPF should significantly increase, which was clearly demonstrated. The same also applies to the process which is described in WO-A-93/11746.

In J. Pharm. Pharmacol. 34: 141–145 (1982), it was furthermore found that the addition of a third powder component to an ordered mixture of salicylic acid (1%) and sucrose formed beforehand can influence the physical stability of ternary mixtures in a different manner as a result of charge interactions. The addition of 0.5–4.0% of magnesium stearate adversely affected the adhesion of the salicylic acid particles to the sucrose carrier, the proportion of weakly bound active compound particles increasing with increasing magnesium stearate concentration. This finding was ascribed to a change in the charge interactions on the surface of the sucrose carrier particles as a result of the positive electrostatic charge of the magnesium stearate and the negative charge of the salicylic acid and sucrose particles. This effect and the fact that the addition of a third component, which preferably adds to the carrier particles, can displace the active compound particles from their adhesion sites has already been pointed out in J. Pharm. Pharmacol. 31: 800 (1979). In contrast, by addition of 2% cornstarch the adhesion of the active compound particles was intensified and the amount of active compound adhering to sucrose was increased, while by addition of 2% of talc the adhesion forces between the particles were generally increased. Similar effects were also found by N. M. Kassem [Thesis DX187842, University of London, 1990] and likewise explained by the electrostatic properties of the constituents.

In WO-A-87/05213, on the other hand, it was proposed to use carriers, consisting of microparticles of a conglomerate of one or more solid water-soluble diluents, such as lactose, xylitol, mannitol, arabinose or dextran, with a lubricant, such as magnesium stearate, sodium benzoate, colloidal silica, hydrogenated oil or fatty substances, for the preparation of inhalation powders. The microparticles preferably have a particle size of 30–150 μm and are prepared by adding the lubricant to an aqueous solution of a part of the solid diluent, granulating the remaining diluent together with this mixture and sieving the granules obtained. The use of such carriers should make possible, inter alia, improved flow properties and improved self-lubricating properties.

However, it has been shown that powder mixtures, in particular interactive powder mixtures, are sensitive to the moisture in the surrounding air. They are therefore only limitedly suitable for use in a multidose dry powder inhaler which contains a powder reservoir, since this is normally not a tight pack in the sense of a hermetic sealing-off of water vapor. This is usually manifested in a dramatic fall in the inhalable proportion of the released dose, which is determined in vitro as the FPD or FPF. The fall is based on a stronger adhesion of the micronized active compound particles to the carrier particles, as from a relative atmospheric humidity of about 60%, as a result of water vapor condensation, "liquid bridges" result in the intermediate spaces which contribute to a stronger binding energy. Visual signs of this process are crust or clump formation, which, however, do not necessarily have to be observed in each case. The process is irreversible, since on drying-up of the liquid bridges "solid bridges" are formed. Inter alia, the water absorption tendency or the water sorption ability of the substances involved is also crucial for the extent of the impairment of the powder properties in the case of high atmospheric humidity storage.

SUMMARY OF THE INVENTION

The invention is therefore based on the object of lowering the sensitivity of powder mixtures to moisture. The object is achieved according to the invention by use of magnesium stearate. It has in fact surprisingly been shown that magnesium stearate is able to minimize the influence of penetrating moisture on the FPD and the FPF during the storage of the inhalation powder, i.e. to prevent or at least considerably to slow down an adverse effect on the FPD and the FPF caused by moisture, and to stabilize the dry powder formulation. The original quality of the pharmaceutical preparation thus remains considerably better than in the case of conventional preparations even on storage under extreme conditions of temperature and humidity. The improvement is usually manifested in that the influence of moisture on the mass median aerodynamic diameter (subsequently also designated as MMAD) and on the accuracy and reproducibility of the released dose can be prevented or greatly slowed. These effects are particularly marked, especially for moisture-sensitive active compounds, since possible hygroscopicity of the active compound favors water absorption and thus the formation of the liquid bridges. Moreover, the use of magnesium stearate as a rule leads to a general improvement in the FPD and the FPF. It is conceivable that the magnesium stearate, in addition to general moisture protection, also stabilizes the carrier materials and active compounds by suppressing or slowing down undesirable morphological phase transitions.

The invention therefore relates to the use of magnesium stearate for improving the resistance to moisture, i.e. for lowering the sensitivity to atmospheric humidity, of dry powder formulations for inhalation. The use of magnesium stearate accordingly brings about an improvement in the storage stability and in particular a reduction of the influence of penetrating moisture on the FPF (and the FPD), which permits the maintenance of a high FPD and FPF even under comparatively extreme temperature and humidity conditions.

DETAILED DESCRIPTION OF THE INVENTION

The dry powder formulations obtainable according to the invention thus comprise a pharmaceutically inactive carrier of noninhalable particle size, a finely divided pharmaceutically active compound of inhalable particle size (i.e. having a mean particle diameter of preferably at most 10 μm, in particular at most 5 μm) and—to improve the resistance to moisture—magnesium stearate, and they are preferably present in the form of "interactive (or ordered or adhesive) mixtures". If desired, the dry powder formulations can also contain a proportion of carrier material of inhalable particle size.

The expression "interactive mixture" or "ordered mixture" or "adhesive mixture" is familiar to the person skilled in the art and in the context of the present invention comprises dry powder formulations in which the pharmacologically inactive carrier is present in a particle size which is noninhalable or mainly noninhalable, and in which microfine active compound particles are bound to the carrier particles by adhesion (i.e. are not contained in the carrier, e.g. in the form of granules).

It has been found that magnesium stearate is suitable for improving the moisture resistance of fundamentally any desired dry powder formulations, independently of the nature of the active compounds and carrier materials. The improvement is particularly marked, however, in the case of dry powders, whose combination of active compound and carrier—i.e. without addition of magnesium stearate—has a high sensitivity to the influence of atmospheric humidity and shows, for example, a decrease in the FPF by at least 50% within 10 days in the case of storage in the open at 40° C. and 75% relative atmospheric humidity. A high sensitivity of the FPF or FPD to atmospheric humidity is frequently observed if the active compound is present in the form of a salt or ester and/or is comparatively hygroscopic or hydrophilic.

An active compound is hygroscopic in this sense if it never completely dries out at a water vapor pressure in the drying air of >0, i.e. in contact with air having a moisture content of >0% relative humidity, but always contains a certain amount of absorptively bound water [H. Sucker, P. Fuchs and P. Speiser: Pharmazeutische Technologie [Pharmaceutical Technology], Georg Thieme Verlag, Stuttgart, New York, 2nd edition 1991, page 85]. The use according to the invention of magnesium stearate is particularly advantageous if the active compound is comparatively hygroscopic and, for example, absorbs or retains at least approximately 0.5% by weight of absorptively bound water on storage in drying air having a relative humidity of 50%.

An active compound powder is hydrophilic if it can easily be wetted by water, in the context of the present invention hydrophilic active compound powders in particular being understood as meaning those which have, for example, a wetting angle of less than 90° [Martin, Swarbrick and Cammarata: Physikalische Pharmazie [Physical Pharmacy], Wissenschaftliche Verlagsgesellschaft mbH, Stuttgart, 3rd edition 1987, page 534]. The use according to the invention of magnesium stearate is particularly advantageous in the case of active compound powders which have a wetting angle of less than 70°.

The use of magnesium stearate for improving the resistance to moisture of dry powder formulations is thus particularly preferred in the case of dry powder formulations which contain a pharmaceutically active compound which is present in the form of a salt or ester and/or absorbs or retains at least approximately 0.5% by weight of absorptively bound water on storage in drying air having a relative humidity of 50% and/or has a wetting angle of less than 90°, in particular less than 70°.

The use according to the invention of magnesium stearate is furthermore especially advantageous for use in multidose dry powder inhalers which contain a powder reservoir from which the individual doses are withdrawn by means of a dosage mechanism. The use of magnesium stearate, however, is also suitable for improving the resistance to moisture of predosed units, which can be present, for example, in the form of capsules.

The active compound present in the formulations obtainable according to the invention can fundamentally be any desired pharmaceutically active compound which can be administered by inhalation in dry powders. In order that the active compound is inhalable, i.e. can pass into the lung, it must be present in particles having a mean particle diameter (measured as MMAD) of at most approximately 10 μm, for example approximately 1 to 10 μm and preferably approximately 1 to 6 μm. Such microfine particles can be obtained in a manner which is known or known per se, for example by micronization, controlled precipitation from suitable solvents (e.g. even from supercritical carbon dioxide) or by spray drying if the process conditions are suitably selected, controlled and carried out.

As active compound, the formulations obtainable according to the invention can preferably contain a beta-mimetic, such as levalbuterol, terbutaline, reproterol, salbutamol, salmeterol, formoterol, fenoterol, clenbuterol, bambuterol, tulobuterol, broxaterol, epinephrine, isoprenaline or hexoprenaline, an anticholinergic, such as tiotropium, ipratropium, oxitropium or glycopyrronium, a corticosteroid, such as butoxicart, rofleponide, budesonide, ciclesonide, mometasone, fluticasone, beclomethasone, loteprednol or triamcinolone, a leukotriene antagonist, such as andolast, iralukast, pranlukast, imitrodast, seratrodast, zileuton, zafirlukast or montelukast, a phosphodiesterase inhibitor, such as filaminast or piclamilast, a PAF inhibitor, such as apafant, forapafant or israpafant, a potassium channel opener, such as amiloride or furosemide, a painkiller, such as morphine, fentanyl, pentazocine, buprenorphine, pethidine, tilidine, methadone or heroin, a potency agent, such as sildenafil, alprostadil or phentolamine, a peptide or protein, such as insulin, erythropoietin, gonadotropin or vasopressin, or a pharmaceutically acceptable derivative or salt of these compounds. In the case of chiral active compounds, this can be present in the form of an optical isomer, a diastereoisomeric mixture of racemate. If desired, the formulations according to the invention can contain two or more pharmaceutically active compounds.

As the moisture sensitivity is frequently a great problem, especially in the case of active compounds which are present as a salt or ester, the use of magnesium stearate is advantageous, in particular in the case of dry powder formulations which contain at least one pharmaceutically active compound in the form of a pharmaceutically acceptable salt, for example a chloride, bromide, iodide, nitrate, carbonate, sulfate, methylsulfate, phosphate, acetate, benzoate, benzenesulfonate, fumarate, malonate, tartrate, succinate, citrate, lactate, gluconate, glutamate, edetate, mesylate, pamoate, pantothenate or hydroxy-naphthoate, or a pharmaceutically active compound in the form of a pharmaceutically acceptable ester, for example an acetate, propionate, phosphate, succinate or etabonate.

The use of magnesium stearate in dry powder formulations which contain a beta-mimetic and/or an anticholinergic and/or a corticosteroid is particularly preferred, and in particular in dry powder formulations which contain a beta-mimetic and/or an anticholinergic and/or a corticosteroid in the form of a pharmaceutically acceptable salt or ester, for example a beta-mimetic in the form of a salt, such as levalbuterol sulfate, formoterol fumarate, formoterol tartrate, salbutamol sulfate or salmeterol xinafoate (salmeterol 1-hydroxy-2-naphthoate), or an anti-cholinergic in the form of a salt, such as oxitropium bromide, glycopyrrolate (glycopyrronium bromide), ipratropium bromide or tiotropium bromide, or a corticosteroid in the form of an ester, such as beclomethasone dipropionate, fluticasone propionate, triamcinolone 16,21-diacetate, triamcinolone acetonide 21-acetate, triamcinolone acetonide 21-disodium phosphate, triamcinolone acetonide 21-hemisuccinate, mometasone furoate or loteprednol etabonate, or a combination thereof, such as ipratropium bromide in combination with salbutamol sulfate.

According to a further preferred aspect, the formulations obtainable according to the invention can in particular also contain a corticosteroid, such as ciclesonide, rofleponide, fluticasone propionate, mometasone furoate or loteprednol etabonate, in combination with a beta-mimetic, such as formoterol fumarate, formoterol tartrate, levalbuterol sulfate or salmeterol xinafoate.

The amount of active compound in the formulations obtainable according to the invention can vary within wide ranges and is to a high extent dependent on the respective active compound and up to a certain degree also on the powder inhaler used. Typically, the active compound concentration can be approximately 0.1 to 10% by weight, in particular approximately 0.1 to 5% by weight, based on the total formulation. Occasionally, higher or lower concentrations can also be expedient, where, however, active compound concentrations of below 0.001% by weight or below 0.01% by weight rarely occur.

For the exact volumetric dosage of most active compounds or formulations, dilution of the active compound with a pharmaceutically inactive excipient is necessary in order to obtain a dosable unit amount meeting the demands on dosage accuracy. For this purpose, the microfine, inhalable active compound particles are mixed with pharmacologically inactive substances (carriers). The dilution is chosen here such that the amount applied from the powder inhaler exactly contains the desired dose. The pharmacologically inactive excipient preferably serves not only for dilution, but also for the adjustment of a flowability of the powder mixture which is as good as possible, and in the case of the "interactive or ordered mixtures" preferably used it is the carrier substance, to which the microfine active compound particles are bonded by adhesion in order thus to achieve and to maintain a suitable mixed material, i.e. homogeneity of the mixture.

The carrier is preferably present in the formulation obtainable according to the invention in a particle size which is not inhalable. The carrier particles, however, should on the other hand not be too large, as this can have a disadvantageous effect on the FPF. The optimum particle size of the carrier employed in this case as a rule depends on the demands and specifications of the powder inhaler which is intended for the administration of the formulation. In the context of the present invention, carriers having customary particle sizes can be used, and optimum particle sizes can easily be determined from case to case by the person skilled in the art. In general, however, the mean particle diameter (MMAD) of the carrier particles can be approximately 10 to 500 μm and preferably approximately 50 to 200 μm.

The adhesion of the active compound particles to the carrier particles should be sufficient that no demixing takes place during processing, transport, storage and dosage operations, but on the other hand not so high that a detachment of the active compound particles which is as quantitative as possible is no longer guaranteed during the dispersion in the inhaler induced by the respiratory flow of the patient. The effectiveness of the release of the active compound particles is especially dependent, in addition to the physicochemical properties of the active compound and the aerodynamic properties of the powder inhaler, on the properties of the carrier, in particular the nature of the carrier and its surface structure, mean particle size and particle size distribution.

In the context of the present invention, fundamentally all carrier materials customarily used in dry powder formulations are suitable, for example mono- or disaccharides, such as glucose, lactose, lactose monohydrate, sucrose or trehalose, sugar alcohols, such as mannitol or xylitol, polylactic acid or cyclodextrin, glucose, trehalose and in particular lactose monohydrate in general being preferred. If desired, the formulations can also contain two or more carrier materials. If desired, in addition to noninhalable carrier particles, the formulation can also contain a proportion of inhalable carrier particles; for example in addition to relatively coarse lactose monohydrate carrier particles it can contain a proportion of, for example, 0.1 to 10% by weight of micronized lactose monohydrate, which can have, for example, a particle size diameter of at most 10 μm, preferably at most 5 μm, for at least 50% of the particles.

The proportion of carrier material in the formulations obtainable according to the invention can vary within a wide range depending on the dilution necessary or desirable for the particular active compound and the amount of magnesium stearate used for improving the resistance to moisture. The proportion of carrier material to the total formulation can be, for example, approximately 80 to 99.9% by weight, where, however, higher or lower proportions can also be advantageous depending on the active compound.

The concentration of magnesium stearate can also vary within relatively wide limits and can be, for example, approximately 0.001 to 10% by weight, in particular approximately 0.01 to 5% by weight, based on the total formulation, a concentration of approximately 0.1 to 2% by weight as a rule being preferred. With a view to toxicological harmlessness, the magnesium stearate concentration, however, will not usually be over approximately 1% by weight, but on the other hand usually at least approximately 0.25% by weight, in order to guarantee a high efficacy, a concentration range of approximately 0.4 to 0.8% by weight, preferably approximately 0.5 to 0.75% by weight, having proven particularly suitable for most cases. The magnesium stearate is preferably employed as a pulverulent material; the particle size is not particularly critical.

If desired, the formulations obtainable according to the invention can contain further components. They preferably consist, however, of one or more pharmaceutically inactive carriers, one or more pharmaceutically active compounds and magnesium stearate.

The dry powder formulations can be prepared according to the invention by mixing together a pharmaceutically inactive carrier of noninhalable particle size (which, if desired, can contain a proportion of inhalable particle size), a finely divided pharmaceutically active compound of inhalable particle size, for example having a mean particle diameter of at most 10 μm (preferably at most 5 μm), and magnesium stearate. In principle, the constituents can be mixed with one another in any desired sequence, where, however, mixing should expediently be carried out in such a way that the particles of the constituents—apart from the adhesion to the carrier particles—are essentially retained as such, i.e. are not destroyed, for example, by granulation and the like. According to a preferred variant, however, a preliminary mixture of magnesium stearate with the carrier can first be prepared and then the active compound particles can be admixed. According to a further preferred variant, a preliminary mixture of the active compound with the carrier can first be prepared and then the magnesium stearate can be admixed. Mixing can be carried out in a manner known per se, for example in a tumble mixer. Preferably, in this process, however, pulverulent magnesium stearate having a mean particle size of approximately 1 to 100 µm, in particular approximately 5 to 20 µm, can be added.

The dry powder formulations described can be used in all customary dry powder inhalers. They are particularly advantageously for use in multidose dry powder inhalers which contain a powder reservoir, in particular in multidose powder inhalers such as described in WO-A-97/20589.

The invention likewise relates to dry powder formulations for inhalation having improved resistance to moisture, comprising a pharmaceutically inactive carrier of noninhalable particle size, a finely divided pharmaceutically active compound in the form of a pharmaceutically acceptable salt or ester of inhalable particle size (preferably having a mean particle diameter of at most 10 μm, in particular at most 5 μm) and 0.25 to 1% by weight, based on the total formulation, of magnesium stearate. Preferred dry powder formulations are those which are present in the form of interactive mixtures. Preferred active compound salts and esters, carrier materials, ranges of amounts, methods and the like follow from the above description.

The invention is illustrated further by the following examples. In the examples, r.h. designates the relative atmospheric humidity; the notation n.d. indicates that the value concerned was not determined. The tests were in each case carried out using a dry powder inhaler of the SkyePharma mDPI type (SkyePharma AG, Switzerland) according to WO-A-97/20589. The FPD and the FPF were determined—if not stated otherwise—in each case using a twin impinger. Screenings were carried out—if not stated otherwise—in each case using a screen having a hole diameter of 180 μm. For the determination of the moisture sensitivity, the dry powders, apart from in example 7, were in each case stored in the open without moisture protection.

EXAMPLE 1

198.46 g of lactose monohydrate having a defined particle size of <200 μm for 100%, <125 μm for 50% and <75 μm for 10% of the particles (screen analysis) are screened and mixed with 1 g of screened magnesium stearate using a tumble mixer. Following this, 0.54 g of formoterol fumarate dihydrate and the preliminary mixture are screened and mixed. The mixture thus obtained is filled into a suitable metering dry powder inhaler. For the exact analytical determination of the particle size distribution and especially of the FPD and/or FPF, an adequate number of doses are released and collected in an impinger or impacter described in the European Pharmacopeia or other national pharmacopeias, e.g. the "twin impinger" or "multi-stage liquid impinger", according to procedures also described there. The active compound particles trapped and deposited are worked up in analytical standard procedures to give sample solutions and the amounts of active compound deposited in each size class are determined. To test the stability to moisture, samples of the inhalation powder are stored in the open at 40° C./75% r.h. or another suitable condition over a period of time of several days to weeks and then tested in the powder inhaler as described above.

The results obtained using the ternary mixture prepared (formulation 1-A) and using conventional mixtures (formulations 1-B and 1-C) in a 5-stage liquid impinger according to Ph. Eur., and the compositions of the mixtures (in % by weight) are listed in table 1. In comparison to the conventional interactive mixtures, the ternary mixture with magnesium stearate, according to the invention, shows the advantage of an increased FPD or FPF and a significantly improved stability of the FPD or FPF on storage at 40° C./75% r.h. As the results for formulation 1-C show, an initial increase in the FPD and FPF can indeed be achieved in conventional formulations by addition of micronized lactose, but not protection against the influence of increased temperature and humidity. This is likewise evident from the MMAD values determined for the formulations 1-A and 1-C immediately after preparation or after 7 or 13 days' storage of the dry powder at 40° C./75% r.h.: for formulation 1-A after preparation 1.8 μm, after 7 days 1.9 μm and after 13 days 1.9 μm; for formulation 1-C after preparation 2.2 μm, after 7 days 4.5 μm and after 13 days 5.5 μm. In contrast to the conventional formulation, the MMAD thus remains constant in the formulation according to the invention, which confirms the results of the FPD and FPF investigation.

TABLE 1

| | Formulation | | |
|---|---|---|---|
| | 1-A | 1-B (comparison) | 1-C (comparison) |
| Lactose monohydrate | 99.23% | 99.73% | 97.24% |
| Lactose monohydrate, micronized | 0.00% | 0.00% | 2.49% |
| Magnesium stearate | 0.50% | 0.00% | 0.00% |
| Formoterol fumarate dihydrate, micronized | 0.27% | 0.27% | 0.27% |
| FPD after preparation [μg per stroke] | 4.7 | 1.3 | 3.3 |
| FPD after 3–4 days at 40° C./75% r.h. [μg per stroke] | 4.5 | n.d. | 1.0 |
| FPF after preparation [% active compound found] | 42.5 | 13.7 | 35.9 |
| FPF after 3–4 days at 40° C./75% r.h. [% active compound found] | 37.3 | n.d. | 11.0 |

EXAMPLE 2

97.23 g of lactose monohydrate having a defined particle size of <200 μm for 100%, <125 μm for 50% and <75 μm for 10% of the particles (screen analysis) are screened and mixed with 2.5 g of screened micronized lactose monohydrate (50% of the particle <5 μm) in a tumble mixer. Following this, 0.27 g of formoterol fumarate dihydrate and the preliminary mixture are sieved and mixed. The mixture thus obtained is mixed with 0.125 g of screened magnesium stearate and filled into a suitable metering dry powder inhaler. For the analytical determination of the FPD or FPF, an adequate number of doses are released and collected in a twin impinger or multi-stage liquid impinger. The active compound particles trapped and deposited are worked up to give sample solutions and the amounts of active compound deposited in each size class are determined. To test the stability to moisture, samples of the inhalation powder are stored in the open at 40° C./75% r.h. for a period of time of a few days and then tested in the powder inhaler as described above.

The results obtained with the prepared mixture (formulation 2) and with a conventional mixture (formulation 1-C) in a 5-stage liquid impinger according to Ph. Eur. and the compositions of the mixtures (in % by weight) are listed in table 2. In comparison to the conventional interactive mixture, the mixture with magnesium stearate, according to the invention, shows the advantage of an increased FPD or FPF and an improved stability of the FPD or FPF on storage at 40° C./75% r.h.

TABLE 2

|  | Formulation | |
| --- | --- | --- |
|  | 2 | 1-C (comparison) |
| Lactose monohydrate | 96.75% | 97.24% |
| Lactose monohydrate, micronized | 2.48% | 2.49% |
| Magnesium stearate | 0.50% | 0.00% |
| Formoterol fumarate dihydrate, micronized | 0.27% | 0.27 |
| FPD after preparation [µg per stroke] | 5.3 | 3.3 |
| FPD after 3–4 days at 40° C./75% r.h. [µg per stroke] | n.d. | 1.0 |
| FPF after preparation [% active compound found] | 41.4 | 35.9 |
| FPF after 3–4 days at 40° C./75% r.h. [% active compound found] | n.d. | 11.0 |

EXAMPLE 3

97 g of lactose monohydrate having a defined particle size of <110 µm for 90%, <70 µm for 50% and <40 µm for 10% of the particles (screen analysis) are screened and mixed with 0.5 g of screened magnesium stearate in a tumble mixer. Following this, 2.5 g of salbutamol sulfate and the preliminary mixture are screened and mixed. The mixture thus obtained is filled into a suitable metering dry powder inhaler. For the analytical determination of the FPD or FPF, an adequate number of doses are released and collected in a twin impinger. The active compound particles trapped and deposited are worked up to give sample solutions and the amounts of active compound deposited in each size class are determined. To test the stability to moisture, samples of the inhalation powder are stored in the open at 40° C./75% r.h. over a period of time of 7 days and then tested in the powder inhaler as described above.

The results obtained with the prepared ternary mixture (formulation 3-A) and with a conventional binary mixture (formulation 3-B) in a twin impinger according to Ph. Eur. and the compositions of the mixtures (in % by weight) are listed in table 3. The ternary mixture with magnesium stearate attains a higher FPD or FPF and is significantly more stable on storage at 40° C./75% r.h.

TABLE 3

|  | Formulation | |
| --- | --- | --- |
|  | 3-A | 3-B (comparison) |
| Lactose monohydrate | 97.00% | 97.50% |
| Magnesium stearate | 0.50% | 0.00% |
| Salbutamol sulfate, micronized | 2.50% | 2.50% |

TABLE 3-continued

|  | Formulation | |
| --- | --- | --- |
|  | 3-A | 3-B (comparison) |
| FPD after preparation [µg per stroke] | 39.5 | 26.2 |
| FPD after 7 days at 40° C./75% r.h. [µg per stroke] | 27.8 | 11.3 |
| FPF after preparation [% active compound found] | 37.4 | 25.3 |
| FPF after 7 days at 40° C./75% r.h. [% active compound found] | 35.6 | 9.7 |

EXAMPLE 4

1 196 g of lactose monohydrate having a defined particle size of <315 µm for 100%, <150 µm for 55–90% and <63 µm for at most 10% of the particles (screen analysis) are screened and mixed with 3 g of screened magnesium stearate in a tumble mixer (tumble blender TB). Following this, 1.44 g of formoterol fumarate dihydrate and the preliminary mixture are screened and mixed. Analogously, with variation of the batch size, the process parameters and the amounts of magnesium stearate and formoterol fumarate, further formulations are prepared in order to investigate their influence on the stability of the FPD. The mixtures obtained are filled—after preparation or after subsequent storage of the open mixture at elevated temperature and humidity—into a suitable metering dry powder inhaler. The in-vitro particle size distribution and the FPD or FPF are determined on an adequate number of doses using a multi-stage liquid impinger.

The results showed that on preparation of the powder mixtures using a tumble mixer virtually only the concentration of magnesium stearate is responsible for the stability with respect to the FPD, while the other parameters in the range investigated were virtually without significance for the stability under increased humidity. In table 4, the batch size, the concentration of magnesium stearate (MS) and the concentration of formoterol fumarate dihydrate (FF) for some representative mixtures and their FPF values measured in a 5-stage liquid impinger according to Ph. Eur., which were obtained immediately after preparation or after storage at 40° C./75% r.h. for 7 days, are compiled. The values indicated are mean values from three determinations each. The results show that the FPF is barely adversely affected any longer by increased temperature and humidity if the magnesium stearate concentration is adequate. The FPF of 32.3% measured for formulation 1-A after 3 weeks' storage at 40° C./75% r.h. moreover appears to indicate that even at a suboptimal magnesium stearate concentration a long-lasting protection against the influence of increased temperature and humidity is achieved.

TABLE 4

| Formulation | Batch size [kg] | MS [% G/G] | FF [% G/G] | FPF after 0 d [%] | FPF after 7 d [%] |
| --- | --- | --- | --- | --- | --- |
| 4-A | 1.2 | 0.25 | 0.12 | 42.5 | 33.6 |
| 4-B | 4.8 | 0.50 | 0.12 | 49.3 | n.d. |
| 4-C | 4.8 | 0.75 | 0.12 | 56.9 | 56.8 |

TABLE 4-continued

| Formulation | Batch size [kg] | MS [% G/G] | FF [% G/G] | FPF after 0 d [%] | FPF after 7 d [%] |
|---|---|---|---|---|---|
| 4-D | 1.2 | 0.25 | 0.34 | 50.0 | 33.5 |
| 4-E | 4.8 | 0.50 | 0.34 | 58.1 | n.d. |
| 4-F | 4.8 | 0.75 | 0.34 | 59.2 | 57.2 |
| 1-C (comparison) | 0.2 | 0.00 | 0.27 | 39.7 | 12.3 |
| 1-A | 0.2 | 0.50 | 0.27 | 44.8 | 32.5 |

EXAMPLE 5

49.5 g of lactose monohydrate having a defined particle size of <200 μm for 100%, <125 μm for 50% and <75 μm for 10% of the particles (screen analysis) are screened and mixed with 0.25 g of screened magnesium stearate in a tumble mixer. Following this, 0.25 g of salbutamol sulfate and the preliminary mixture are screened and mixed. Analogously, with variation of the concentration of magnesium stearate (MS) and salbutamol sulfate (SS), further mixtures are prepared according to table 5. The mixtures obtained are filled immediately after preparation or after storage at 40° C./75% r.h. for 5 or 21 days into a suitable metering dry powder inhaler. For the determination of the FPD or FPF, an adequate number of doses are released in a twin impinger according to Ph. Eur., collected and the active compound content of the individual fractions is determined analytically.

The FPF values indicated in table 5 (mean values of two measurements) shows that magnesium stearate brings about protection against increased temperature and humidity even in the case of the moisture-sensitive active compound salbutamol sulfate, but stabilization of the FPF is only achieved at higher magnesium stearate concentrations than in the case of the formoterol fumarate preparations.

TABLE 5

| Formulation | MS [% G/G] | SS [% G/G] | FPF [%] after 0 d | 5 d | 7 d |
|---|---|---|---|---|---|
| 5-A | 0.5 | 0.5 | 9.3 | 14.2 | 12.0 |
| 5-B | 0.5 | 1.0 | 22.3 | 17.1 | 14.9 |
| 5-C | 0.5 | 2.5 | 30.2 | 25.6 | 22.3 |
| 5-D | 1.0 | 0.5 | 19.0 | 18.8 | 13.5 |
| 5-E | 1.0 | 1.0 | 23.0 | 20.1 | 15.8 |
| 5-F | 1.0 | 2.5 | 25.0 | 22.6 | 20.8 |
| 5-G | 2.5 | 1.0 | 22.7 | 23.4 | 21.5 |
| 5-H | 2.5 | 2.5 | 25.9 | 26.4 | 27.4 |
| Comparison: | | | | | |
| 5-I | 0.00 | 0.5 | 13.5 | 5.3 | 4.0 |
| 5-J | 0.00 | 1.0 | 19.7 | 9.5 | 6.6 |
| 5-K | 0.00 | 2.5 | 25.3 | 14.8 | 13.9 |

EXAMPLE 6

99.2 g of lactose monohydrate having a particle size of <315 μm for 100%, <150 μm for 55–90% and <63 μm for at most 10% of the particles (screen analysis) are screened and mixed with 0.5 g of screened magnesium stearate in a tumble mixer. Following this, 0.34 g of tiotropium bromide and the preliminary mixture are screened and mixed. The mixture obtained is filled after preparation or storage at 40° C./75% r.h. 15 for 7 days into a suitable metering dry powder inhaler. For the determination of the FPD or FPF, an adequate number of doses are released and collected in a multi-stage impinger according to Ph. Eur. and the active compound content of the individual fractions is determined analytically. The samples filled immediately after preparation showed an FPF of 8.0 μg and an FPF of 48.4% (mean values of 2 measurements); for the samples stored for 7 days under moist conditions, an FPD of 6.9 μg and an FPF of 43.0% were obtained (mean values of 4 measurements), i.e. stabilization with 0.5% magnesium stearate produces a sufficiently uniform FPD or FPF even in the case of the moisture-sensitive tiotropium bromide.

EXAMPLE 7

For the investigation of the influence of increased humidity and temperature on formulations according to the invention under conditions near to those in practice, dry powder inhalers of the SkyePharma mDPI type (SkyePharma AG, Switzerland), were filled, according to the disclosure of WO-A-97/20589, with 2 g each of dry powder, freshly prepared according to example 1, consisting of 99.23% by weight of lactose monohydrate, 0.50% by weight of magnesium stearate and 0.27% by weight of micronized formoterol fumarate dihydrate (formulation 1-A). The in-vitro data were determined immediately after filling and after 3, 6 and 12 months' storage of the unpacked inhalers without moisture protection under various temperature and humidity conditions. The doses released and the stroke masses were determined by means of strokes Nos 2–4, 149–152 and 298–300 from three inhalers each, which were released into a Buchner funnel according to the method described by Collins at the Conference Drug Delivery to the Lungs VIII, London, December 1998 (meeting reports pages 116–119). The FPD or FPF was determined at 60 l/min by means of a 5-stage liquid impacter according to Ph. Eur. with the aid of strokes Nos 6–15 and 287–296 from three inhalers each. The mean values and relative standard deviations compiled in table 6 show that the formulation according to the invention is barely adversely affected over long periods of time even under comparatively extreme temperature and humidity conditions.

TABLE 6

| Storage | Stroke mass [mg] | Released dose [μg] | FPF [%] | FPD [μg] |
|---|---|---|---|---|
| none | 6.0 (±5.4%) | 10.2 (±10.1%) | 43.5 | 6.0 |
| 25° C./60% r.h.: | | | | |
| 3 months | 6.1 (±4.8) | 10.5 (±9.5%) | 40.8 | 5.4 |
| 6 months | 5.9 (±8.2%) | 10.9 (±6.9%) | 47.8 | 7.0 |
| 12 months | 6.1 (±5.0%) | 12.1 (±5.9%) | 42.2 | 5.9 |
| 30° C./70% r.h.: | | | | |
| 3 months | 6.1 (±6.9) | 11.0 (±12.9%) | 40.1 | 5.6 |
| 6 months | 6.2 (±8.7%) | 10.6 (±11.5%) | 39.9 | 5.7 |
| 12 months | 6.3 (±4.3%) | 10.7 (±5.9%) | 42.0 | 5.7 |
| 40° C./75% r.h.: | | | | |
| 3 months | 5.8 (±9.7) | 9.9 (±9.8%) | 38.1 | 5.2 |

TABLE 6-continued

| Storage | Stroke mass [mg] | Released dose [µg] | FPF [%] | FPD [µg] |
| --- | --- | --- | --- | --- |
| 6 months | 6.0 (±19.5%) | 10.3 (±19.2%) | 35.1 | 4.9 |
| 12 months | 6.7 (±6.8%) | 10.7 (±7.9%) | 37.9 | 5.4 |

EXAMPLE 8

Analogously to example 4, a dry powder consisting of 0.2% by weight of formoterol fumarate dihydrate, 0.5% by weight of glycopyrrolate, 0.5% by weight of magnesium stearate and 98.8% by weight of lactose monohydrate was prepared.

We claim:

1. A method of producing a dry powder formulation for inhalation, said formulation having a fine particle fraction (FPF) with reduced sensitivity to penetrating moisture, and comprising a pharmaceutically inactive carrier comprising particles of noninhalable size and a pharmaceutically active component comprising at least one finely-divided pharmaceutically active compound comprising particles of inhalable size; said method comprising: mixing together (i) said pharmaceutically inactive carrier; (ii) said pharmaceutically active component; and (iii) pulverulent magnesium stearate, in an amount of 0.1 to 2% by weight, based on the total weight of the formulation, said amount being effective to provide the FPF with reduced sensitivity to penetrating moisture and to stabilize the dry powder formulation.

2. The method of claim 1, comprising mixing by tumble blending.

3. The method of claim 1, comprising first mixing the carrier with the magnesium stearate and then admixing the pharmaceutically active component therewith.

4. The method of claim 1, comprising first mixing the carrier with the pharmaceutically active component and then admixing the magnesium stearate therewith.

5. The method of claim 1, wherein the pharmaceutically active compound is a hygroscopic compound capable of absorbing at least 0.5% by weight of its own weight of absorptively bound water when stored in air having a relative humidity of 50%.

6. The method of claim 1, wherein the pharmaceutically active compound is a hydrophilic compound having a wetting angle of less than 90°.

7. The method of claim 1, wherein the pharmaceutically active compound is a hydrophilic compound having a wetting angle of less than 70°.

8. The method of claim 1, wherein the pharmaceutically active compound is formoterol or a pharmaceutically acceptable salt thereof.

9. The method of claim 1, wherein the pharmaceutically active compound is selected from the group consisting of formoterol fumarate, formoterol tartrate, ipratropium bromide and tiotropium bromide.

10. The method of claim 1, wherein the pharmaceutically active component further comprises a second pharmaceutically active compound having particles of inhalable size.

11. The method of claim 10, wherein the pharmaceutically active component comprises a) a compound selected from the group consisting of formoterol fumarate, formoterol tartrate, levalbuterol sulfate and salmeterol xinafoate, and b) a corticosteroid.

12. The method of claim 1, wherein the pharmaceutically active compound has a mean particle size of 1 to 10 µm.

13. The method of claim 1, wherein the pharmaceutically active compound has a mean particle size of 1 to 6 µm.

14. The method of claim 1, wherein the magnesium stearate is present in an amount of 0.25 to 1% by weight, based on the total weight of the formulation.

15. The method of claim 1, wherein the magnesium stearate is present in an amount of 0.4 to 0.8% by weight, based on the total weight of the formulation.

16. The method of claim 1, wherein the carrier is selected from the group consisting of monosaccharides, disaccharides, sugar alcohols, polylactic acid and cyclodextrin.

17. The method of claim 1, wherein the carrier is selected from the group consisting of glucose, lactose monohydrate and trehalose.

18. The method of claim 1, wherein the carrier particles have a mass mean aerodynamic diameter of 10 to 500 µm.

19. The method of claim 1, wherein the carrier particles have a mass mean aerodynamic diameter of 50 to 200 µm.

20. The method of claim 1, further comprising admixing particles of micronized lactose monohydrate wherein at least 50% of the particles thereof have a maximum particle size of 10 µm, with said carrier, said pharmaceutically active component and said magnesium stearate.

21. A method of stabilizing a fine particle fraction (FPF) of a dry powder formulation for inhalation, said formulation comprising a pharmaceutically inactive carrier and a finely-divided pharmaceutically active compound; said method comprising: mixing said carrier having particles of noninhalable particle size, said pharmaceutically active compound having particles of inhalable particle size and pulverulent magnesium stearate, an amount of 0.1 to 2% by weight, based on the total weight of the formulation, said amount being effective to stabilize the FPF of the formulation against penetrating moisture.

22. A dry powder formulation for inhalation, comprising:

a) a pharmaceutically inactive carrier having particles of noninhalable particle size, b) at least two finely divided pharmaceutically active compounds having particles of inhalable particle size, and c) magnesium stearate adhering to said particles of said pharmaceutically inactive carrier, the magnesium stearate being in an amount of 0.1 to 2% by weight, based on the total weight of the formulation, said amount being sufficient to provide the formulation with an improved resistance to moisture.

23. The formulation of claim 22, wherein one pharmaceutically active compound is selected from the group consisting of formoterol fumarate, formoterol tartrate, levalbuterol sulfate and salmeterol xinafoate, and a second pharmaceutically active compound is a corticosteroid.

24. The formulation of claim 22, wherein the magnesium stearate is present in an amount of 0.25 to 1% by weight, based on the total weight of the formulation.

25. The formulation of claim 22, further comprising particles of micronized lactose monohydrate wherein at least 50% of the particles thereof have a maximum particle size of 10 µm.

26. The method of claim 1, wherein said formulation exhibits a reduction in FPF by at least 50% within 10 days of storage at 40° C. and 75% relative atmospheric humidity.

27. The method of claim 21, wherein said formulation exhibits a reduction in FPF by at least 50% within 10 days of storage at 40° C. and 75% relative atmospheric humidity.

28. The formulation of claim 22, said formulation comprising a fine particle fraction (FPF) and exhibiting a reduction in said FPF by at least 50% within 10 days of storage at 40° C. and 75% relative atmospheric humidity.

* * * * *